(12) United States Patent
Bechtold et al.

(10) Patent No.: US 8,308,632 B2
(45) Date of Patent: Nov. 13, 2012

(54) METHOD AND APPARATUS FOR DISPLAYING INFORMATION IN MAGNETICALLY GUIDED CAPSULE ENDOSCOPY

(75) Inventors: Mario Bechtold, Hemhofen (DE); Aleksandar Juloski, Nuremberg (DE); Hironao Kawano, Tokyo (JP); Rainer Kuth, Hoechstadt (DE)

(73) Assignees: Siemens Aktiengesellschaft, Munich (DE); Olympus Medical Systems Corporation, Tokyo (JP)

( * ) Notice: Subject to any disclaimer, the term of this patent is extended or adjusted under 35 U.S.C. 154(b) by 220 days.

(21) Appl. No.: 12/815,584

(22) Filed: Jun. 15, 2010

(65) Prior Publication Data

US 2011/0306830 A1    Dec. 15, 2011

(51) Int. Cl.
*A61B 1/00*    (2006.01)
(52) U.S. Cl. .................................. 600/117; 600/114
(58) Field of Classification Search ............... 600/117, 600/118, 424, 114
See application file for complete search history.

(56) References Cited

U.S. PATENT DOCUMENTS

| | | | |
|---|---|---|---|
| 5,681,260 A | 10/1997 | Ueda et al. | |
| 7,173,507 B2 | 2/2007 | Ries | |
| 7,182,089 B2 | 2/2007 | Ries | |
| 7,343,036 B2 | 3/2008 | Kleen et al. | |
| 2002/0188174 A1 | 12/2002 | Aizawa et al. | |
| 2003/0060702 A1 | 3/2003 | Kuth et al. | |
| 2007/0225550 A1* | 9/2007 | Gattani et al. | 600/101 |
| 2009/0033742 A1 | 2/2009 | Jensen | |
| 2009/0227840 A1* | 9/2009 | Uchiyama et al. | 600/118 |
| 2009/0227864 A1* | 9/2009 | Sato et al. | 600/424 |
| 2009/0299142 A1* | 12/2009 | Uchiyama et al. | 600/118 |
| 2010/0010305 A1* | 1/2010 | Kawano | 600/118 |
| 2010/0010306 A1* | 1/2010 | Kawano et al. | 600/118 |
| 2010/0030026 A1* | 2/2010 | Uchiyama et al. | 600/118 |
| 2010/0234685 A1 | 9/2010 | Juloski et al. | |
| 2011/0130649 A1* | 6/2011 | Strommer et al. | 600/424 |

FOREIGN PATENT DOCUMENTS

| | | |
|---|---|---|
| EP | 2 116 169 | 11/2009 |
| WO | WO 2008/099851 | 8/2008 |

OTHER PUBLICATIONS

U.S. Appl. No. 12/724,597, filed Mar. 16, 2010.

* cited by examiner

*Primary Examiner* — John P Leubecker
(74) *Attorney, Agent, or Firm* — Schiff Hardin LLP

(57) ABSTRACT

A magnetically guided endoscope system has a display system wherein the position of the boundary of the examination region of the magnetic field that is used for capsule endoscope guidance is displayed and/or the position of the peak of the magnetic field used for capsule guidance is displayed. The displayed information can be presented in the form of computer-generated graphics superimposed on a camera image of the patient by a computer, or can be a fixed indicator on the display screen of a display at which a computer causes the camera image of the patient to be displayed at a position that is correctly oriented with respect to the fixed information.

9 Claims, 2 Drawing Sheets

METHOD AND APPARATUS FOR DISPLAYING INFORMATION IN MAGNETICALLY GUIDED CAPSULE ENDOSCOPY

BACKGROUND OF THE INVENTION

1. Field of the Invention

The present invention concerns magnetically guided capsule endoscope, and in particular concerns a method and apparatus for displaying relevant information during the course of a magnetic guided capsule endoscope procedure.

2. Description of the Prior Art

Magnetically guided capsule endoscopy is a known medical procedure for undertaking different types of medical examinations and procedures inside of a patient. For this purpose, the patient swallows a small capsule, which proceeds through the patient's digestive system. When the capsule is located in a relevant region of the patient, the desired procedure can be implemented, such as imaging, administration of therapy, minimal surgical procedures, etc. After the procedure is completed, the capsule continues through the digestive tract of the patient and is eliminated naturally.

As the capsule proceeds through the digestive tract of the patient, it is subjected to naturally occurring physiological forces, such as due to peristalsis. Additionally, however, it is possible to directionally guide the capsule within the body of the patient by magnetic means. Several alternatives are known for such magnetic guidance. For example, the capsule itself can be provided with a permanent magnet, and a magnetic field can be created in which the examination subject is located. The magnetic field is adjustable in strength and orientation, so that the permanent magnet, or magnetic material within the capsule is then caused to move within the magnetic field.

Another known alternative is to provide the capsule itself with actively controllable magnetic coils, which can then interact with a field in which the patient is located.

Regardless of the type of magnetic guidance that is employed, it is useful for the physician who is tracking the procedure to be able to obtain certain information regarding the operation of the magnetic guidance system and/or the position of the capsule within the patient, in particular the position of the patient within the examination volume (in which the magnetic field is most uniform and accurate guidance is thus most predictable) of the apparatus that is used for magnetic guidance.

Although systems are known that allow pictorial or graphics information to be displayed that schematically show the position of the capsule within the body of the patient, such systems do not provide the physician with information concerning the relation of the current position of the capsule to the boundary of the examination volume. Moreover, most magnetic guidance systems operate by causing a peak field to be generated at a particular location within the subject, the position of this peak field being variable in order to achieve the aforementioned guidance. Current systems do not provide information to this system regarding the location of this peak field in relation to the current position of the patient.

SUMMARY OF THE INVENTION

It is an object of the present invention to provide a method and apparatus for providing a physician with the aforementioned types of information in real time while conducting a magnetically guided endoscope procedure.

The above object is achieved in accordance with the present invention in a method for displaying information in real time during a magnetically guided endoscope procedure wherein at least one camera is provided in the apparatus used for magnetic guidance, this camera generating a camera image of the exterior of the patient during the procedure. This image from the camera is displayed by a host computer at a display device, and relevant information concerning the magnetic guidance system is simultaneously presented to the physician at the display, superimposed on the camera image of the exterior of the patient.

The superimposed information regarding the magnetic guidance system may be the boundaries of the examination region and/or the current location of the magnetic peak field.

The superimposition can be achieved electronically (computationally) by the host computer, by generating and superimposing a graphics representation of the examination volume and/or the location of the peak field.

Alternatively, the display screen of the display device may have a fixed representation of the shape and size of the examination volume thereon and/or an indicator (such as a dot or a cross) that is used to indicate the position of the magnetic peak field. The host computer then suitably adjusts (moves) the displayed camera image, according to information supplied to the computer concerning the position of the examination volume and/or the position of the peak field in order to cause the patient image to be superimposed with the fixed representation to show the correct, real-time relationship on the camera image of the patient.

With a suitable wide-angle lens, it may suffice to use one centrally located camera in the magnetic guidance apparatus. Preferably, however, multiple cameras are used, such as four cameras respectively located at four corners of the patient receptacle of the apparatus. The respective images from the multiple cameras can then be combined in the host computer to form a complete overview image of the exterior of the patient in the magnetic guidance system, which is superimposed with the aforementioned information.

DESCRIPTION OF THE PREFERRED EMBODIMENTS

Figure 1:
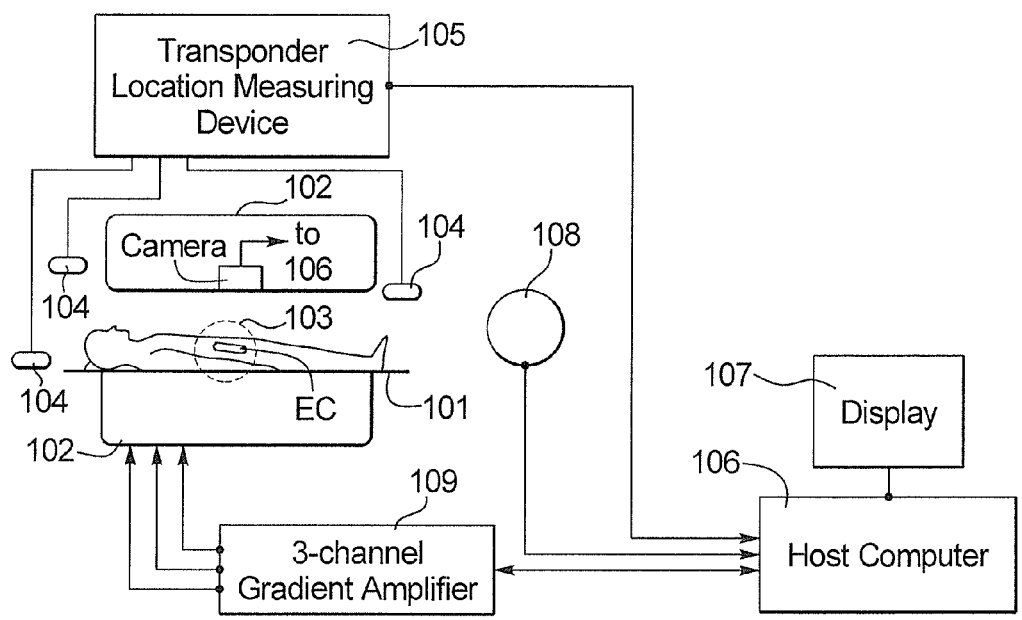
FIG. 1 schematically illustrates a magnetically guided endoscope apparatus constructed and operating in accordance with the present invention.

The basic components of a magnetically guided endoscope system are schematically illustrated in FIG. 1. The system includes a magnetic field generator 102 in which a patient P is received. In a known manner, the magnetic field generator 102 generates a magnetic field, preferably a three-dimensionally controllable magnetic field. The magnetic field is generated by respective coils (not shown) located within the field generator 102, that are respectively supplied with currents by a three-channel gradient amplifier 109. The coils are oriented so as to be able to generate three orthogonally oriented magnetic fields, such as three magnetic fields respectively oriented according to the axes of a Cartesian coordinate system.

For this purpose, the gradient amplifier 109 is operated by a host computer 106 in a known manner. Such operation may be as described, for example, in one or more of U.S. Pat. Nos. 7,343,036 and/or 7,182,089 and/or 7,173,507. The teachings of all three of those United States patents are incorporated herein by reference.

For implementing an endoscope procedure, an capsule endoscope EC (not shown to scale in FIG. 1) is swallowed by the patient P, and the capsule endoscope EC proceeds through the digestive tract of the patient P. Dependent on the arrangement of the coils within the magnetic field generator 102, the magnetic field generated thereby is most uniform and most precisely defined in an examination region 103 of the magnetic field generator 102. For implementing the endoscope procedure, the patient P is positioned by adjustment of a patient platform 101, on which the patient P lies, within the magnetic field generator 102, so that the examination region 103 encompasses the region within the patient P in which it is desired to implement the procedure. Of course, it is also possible to continuously adjust the position of the patient platform 101 and the patient P thereon as the capsule endoscope EC proceeds through the digestive tract of the patient P, so that the capsule endoscope EC is always located within the examination region 103.

For identifying the position of the capsule endoscope, a position detector 105 is provided, that is connected to a number of sensors 104. Such position detection can proceed in any of a number of known ways, such as by providing the capsule endoscope with a transponder (not shown) that emits signals that are detected by the sensors 104, or by providing any type of detectable component, such as a permanent magnet, or ferromagnetic material, that can be identified/detected by the sensors 104. Three-dimensional position information regarding the real-time position of the capsule endoscope EC within the patient P thus can be obtained. This information is supplied to the host computer 106.

Usually, it is possible, simply by knowing the currents that are supplied to the respectively coils of the magnetic field generator 102, to mathematically calculate the boundaries of the examination region 103, as well as the absolute location within the magnet field generator 102 of the peak of the magnetic field generated by each coil and/or the peak of the total magnetic field that results from the superimposition of the three orthogonal magnetic fields. Alternatively, or as a redundant verification, a field detector 108 can be provided, at least for detecting the location of the magnetic peak field. The field detector 108 provides a signal representing at least the position of the magnetic peak field to the host computer 106.

In the embodiment shown in FIG. 1, a camera 110 is provided in the magnet field generator 102 that generates a camera (static or dynamic) image of the patient P, or at least a designated portion of the patient P. The camera image shows the exterior of the patient P.

Figure 2:
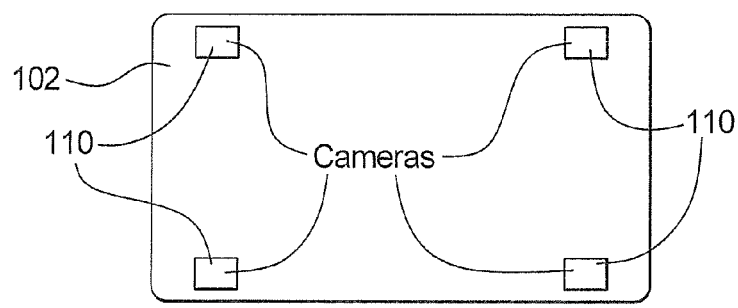
FIG. 2 illustrates a camera arrangement in an alternative embodiment to the use of a single camera shown in FIG. 1.

As an alternative to the use of a single camera 110 shown in FIG. 1, multiple cameras 110 can be used, as schematically illustrated in the embodiment of FIG. 2, showing the use of four such cameras. Any suitable number of cameras, however, may be appropriate. When multiple cameras 110 are used, the host computer 106, in a known manner, combines the respective images generated by the cameras 110 at the respective edges thereof, in order to form a complete image of the patient P.

The camera image of the patient P is caused by the host computer 106 to be displayed at a display 107 in communication with the host computer 106.

Figure 3:
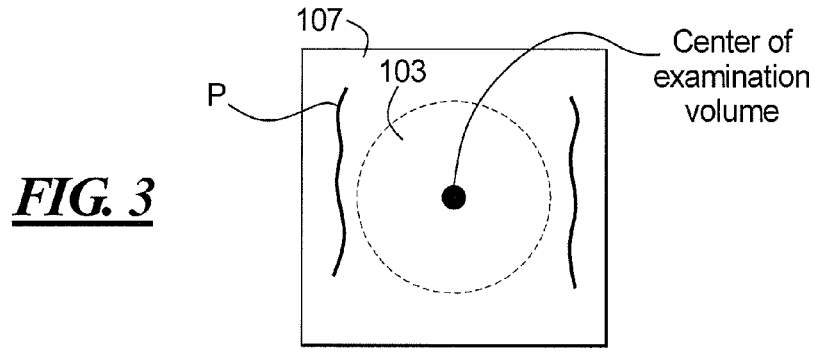
FIG. 3 schematically illustrates a display with the indicators of the examination region presented thereon in accordance with the present invention.

As schematically shown in FIG. 3, a presentation is also shown at the display 107 that indicates the position of the boundary and/or the center of the examination region 103 relative to the camera image of the patient P.

Figure 4:
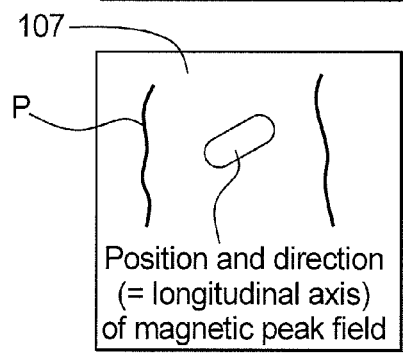
FIG. 4 schematically illustrates a display with the indicators of the magnetic peak field presented thereon in accordance with the present invention.

As schematically shown in FIG. 4, a presentation is also shown at the display 107 that indicates the position and/or direction of the capsule endoscope which is(are) presumed from the magnetic peak field detected by the field detector 108 or the operating information of the host computer 106 to generate the magnetic peak field by a graphical capsule endoscope relative to the camera image of the patient P. The longitudinal axis of the graphical capsule endoscope shows the presumed direction of the capsule endoscope and the position of the graphical capsule endoscope shows the presumed position of the capsule endoscope.

Figure 5:
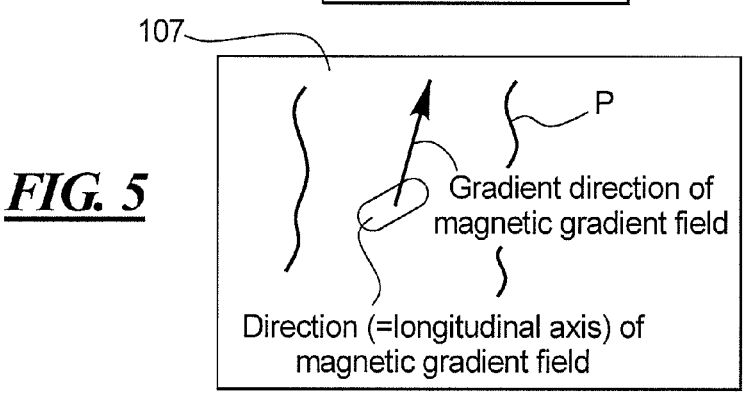
FIG. 5 schematically illustrates a display with the indicators of the magnetic gradient field presented thereon in according with present invention, FIG. 6 schematically illustrates a display with the indicators of the information detected by position detector presented thereon in according with present invention.

As schematically shown in FIG. 5, a presentation is also shown at the display 107 that indicates the direction of the capsule endoscope and the gradient direction of magnetic gradient field, which are presumed from the magnetic gradient field detected by the field detector 108 or the operating information of the host computer 106 to generate the magnetic gradient field, by a graphical capsule endoscope and an graphical arrow relative to the camera image of the patient P. The longitudinal axis of the graphical capsule endoscope shows the presumed direction of the capsule endoscope and the graphical arrow shows the gradient direction of the magnetic gradient field.

Figure 6:
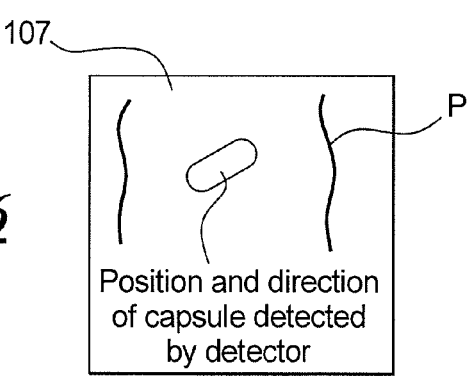

As schematically shown in FIG. 6, a presentation is also shown at the display 107 that indicates the position and direction of the capsule endoscope, which are detected by the position detector 105, by a graphical capsule endoscope relative to the camera image of the patient P. The longitudinal axis of the graphical capsule endoscope shows the detected direction of the capsule endoscope and the position of the graphical capsule endoscope shows the detected position of the capsule endoscope.

The presentation of the indicators (boarder and center) of the examination region 103 and/or the indicators of the peak of the magnetic field and/or indicators of the magnetic gradient field and/or indicators of information detected by position detector 105 can ensue graphically, by means of graphics generated by the host computer 106 and electronically superimposed with the camera image of the patient P at the display 107. Alternatively, the presentation can ensue by means of a fixed indicators of the examination region 103 on the screen of the display 107. In this latter alternative, the host computer 106 then positions the camera image of the patient P on the screen 107 at an appropriate location so that the camera image of the patient P is accurately positioned "beneath" either the indicators of the examination region 103.

The necessary information for superimposing the graphics and positioning the camera image of the patient P is provided to the host computer 106 by the position detector 105 and/or the field detector 108 and/or the gradient amplifier 109 and/or the host computer 106 itself.

Particularly in the embodiment wherein the host computer 106 provides the graphical indicators of the examination region 103 and/or the graphical indicators of the peak of the magnetic field and/or indicators of the magnetic gradient field and/or indicators of the information detected by position detector 105, the indicators of multiple items (example: the examination region 103 and the peak of the magnetic field) can be simultaneously presented at the display 107.

Although modifications and changes may be suggested by those skilled in the art, it is the intention of the inventors to embody within the patent warranted hereon all changes and modifications as reasonably and properly come within the scope of his contribution to the art.

We claim as our invention:

1. A method for displaying information in a magnetically guided endoscopy procedure, comprising the steps of:
    with a magnetic guidance system, magnetically guiding an capsule endoscope in vivo through a patient undergoing an endoscopy procedure, using a magnetic field generated by the magnetic guidance system that has an examination volume, and a magnetic field peak or a magnetic gradient field, said capsule endoscope being at a position in the patient;
    obtaining a camera image of an exterior of the patient in the magnetic guidance system;
    independently of said position of said capsule endoscope, detecting spatial information identifying at least one of said examination volume, said magnetic field peak, or said magnetic gradient field;
    automatically identifying, in a computer supplied with said spatial information and said camera image, an indicator of the examination volume, an indicator of the magnetic peak field, or an indicator of the magnetic gradient field relative to said camera image; and
    from said computer, causing said camera image of the patient to be shown at a display simultaneously with a presentation superimposed with the camera image of the patient that indicates, on said camera image of the patient, at least one of said indicator of the examination region, said indicator of said magnetic peak field, and said indicator of the magnetic gradient field.

2. A method as claimed in claim 1 comprising obtaining said camera image with a single camera.

3. A method as claimed in claim 1 comprising obtaining respective sub-images of the patient in the magnetic guidance system with a plurality of cameras and, in said computer, combining said sub-images to form said camera image of the patient.

4. A method as claimed in claim 1 comprising generating said presentation graphically in said computer as a graphics display, and superimposing said graphics display on said camera image of the patient at said display.

5. A method as claimed in claim 1 comprising generating said presentation as a fixed visual indicator of said information on a screen of said display, and, via said computer, positioning said camera image of the patient at said display screen relative to said fixed indicator.

6. A display system for a magnetically guided endoscopy system, comprising:
    a detector that detects with spatial information independently of said position of said capsule endoscope, representing an indicator of an examination region of said magnetic field, and/or with information representing an indicator of a peak of said magnetic field, and/or with information representing an indicator of a gradient of said magnetic field;
    a camera system that generates a camera image of the patient undergoing the endoscope procedure;
    a computer supplied with said spatial information and said camera image;
    a display in communication with said computer; and
    said computer being configured to generate a graphics presentation providing a graphics indicator selected from the group consisting of an indicator of the examination region and an indicator of the magnetic peak field and an indicator of the magnetic gradient field, said computer being configured to present said camera image at said display superimposed with said graphics indicator.

7. A system as claimed in claim 6 wherein said camera system comprises a single camera.

8. A system as claimed in claim 7 wherein said camera system comprises a plurality of cameras that respectively obtain sub-images of the patient, and wherein said computer is configured to combine said sub-images to generate said camera image of the patient that is displayed at said display.

9. A display system for a magnetically guided endoscope system, comprising:
    a detector that detects spatial information representing a boundary and/or a center of an examination region of a magnetic field in which a patient is situated while undergoing an endoscopy procedure in which a capsule endoscope is guided in vivo by interaction with said magnetic field, said detector detecting said spatial information independently of a position of the capsule endoscope in the patient;
    a camera system that obtains a camera image of the patient undergoing the endoscope procedure;
    a computer supplied with said spatial information and said camera image;
    a display having a display screen with a fixed indicator thereon of said boundary and/or said center of the examination region; and
    said computer being configured to display said camera image of the patient at said display at a position on said display that causes said fixed indicator of said boundary and/or said center of said examination region to correctly show boundary and/or center of the examination region relative to said camera image.

* * * * *